United States Patent
Dekker et al.

(10) Patent No.: US 9,426,435 B2
(45) Date of Patent: *Aug. 23, 2016

(54) SCANNING LASER PROJECTOR

(71) Applicant: Octrolix BV, Enschede (NL)

(72) Inventors: Ronald Dekker, Enschede (NL); Edwin Jan Klein, Enschede (NL)

(73) Assignee: Octrolix BV (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,641

(22) Filed: Mar. 9, 2015

(65) Prior Publication Data

US 2015/0189245 A1 Jul. 2, 2015

Related U.S. Application Data

(63) Continuation of application No. 14/479,665, filed on Sep. 8, 2014, now Pat. No. 9,025,911, which is a continuation of application No. 13/289,422, filed on Nov. 4, 2011, now Pat. No. 8,855,447, which is a
(Continued)

(51) Int. Cl.
*G02B 6/12* (2006.01)
*H04N 9/31* (2006.01)
(Continued)

(52) U.S. Cl.
CPC ............. *H04N 9/3129* (2013.01); *A61B 5/489* (2013.01); *G02B 6/12007* (2013.01);
(Continued)

(58) Field of Classification Search
CPC ................................................ G02B 6/12004
See application file for complete search history.

(56) References Cited

U.S. PATENT DOCUMENTS

| | | | |
|---|---|---|---|
| 4,146,297 | A | 3/1979 | Alferness et al. |
| 5,559,913 | A | 9/1996 | Lerminiaux |

(Continued)

FOREIGN PATENT DOCUMENTS

| | | |
|---|---|---|
| JP | 0560928 A | 3/1993 |
| WO | 0205000 A2 | 1/2002 |

(Continued)

OTHER PUBLICATIONS

Mangeat et al., "Integrated polarization rotator made of periodic asymmetric buried Ta2O5/silica sol-gel waveguides", "Optics Express", Sep. 17, 2007, pp. 12436-12442, vol. 15, No. 19, Publisher: Optical Society of America, Published in: US.

(Continued)

*Primary Examiner* — Ryan Lepisto
*Assistant Examiner* — Mary A El Shammaa
(74) *Attorney, Agent, or Firm* — Kaplan Breyer Schwarz & Ottesen, LLP

(57) ABSTRACT

A scanning projector suitable for projecting an image comprising a plurality of wavelength signals (i.e., light signals having different wavelengths) is disclosed. Embodiments of the present invention comprise a beam combiner comprising a planar lightwave circuit that includes a plurality of surface waveguides arranged in define a plurality of input ports, a mixing region, and an output port. Different wavelength signals received at the input ports are combined into a composite output beam that is scanned over a region. The projector (1) scans a first wavelength signal over a plurality of image points in the region, (2) detects an amount of the first wavelength signal reflected from each image point, whose reflectivity at the first wavelength is based on a measurand, and (3) projects an image onto the region using a second wavelength signal, where the image is based on the reflected first wavelength signal at each of the image points.

28 Claims, 8 Drawing Sheets

Related U.S. Application Data continuation-in-part of application No. 13/208,806, filed on Aug. 12, 2011, now Pat. No. 8,965,156.

(60) Provisional application No. 61/344,553, filed on Aug. 19, 2010, provisional application No. 61/376,483, filed on Aug. 24, 2010, provisional application No. 61/477,960, filed on Apr. 21, 2011.

(51) Int. Cl.

| | |
|---|---|
| *G03B 21/20* | (2006.01) |
| *G03B 33/06* | (2006.01) |
| *G03B 33/12* | (2006.01) |
| *A61B 5/00* | (2006.01) |
| *G02B 6/293* | (2006.01) |

(52) U.S. Cl.
CPC ......... *G03B 21/2033* (2013.01); *G03B 33/06* (2013.01); *G03B 33/12* (2013.01); *A61B 5/0062* (2013.01); *A61B 5/4887* (2013.01); *G02B 6/12004* (2013.01); *G02B 6/29388* (2013.01); *G02B 2006/12035* (2013.01)

(56) References Cited

U.S. PATENT DOCUMENTS

| | | | |
|---|---|---|---|
| 5,854,868 | A | 12/1998 | Yoshimura et al. |
| 6,212,310 | B1 | 4/2001 | Waarts et al. |
| 6,318,863 | B1 | 11/2001 | Tiao et al. |
| 7,318,644 | B2 | 1/2008 | Abu-Ageel |
| 7,413,311 | B2 | 8/2008 | Govorkov et al. |
| 7,575,326 | B2 | 8/2009 | Nishida et al. |
| 7,978,189 | B2 | 7/2011 | Sprague et al. |
| 2003/0002786 | A1 | 1/2003 | Ooyama et al. |
| 2003/0025842 | A1 | 2/2003 | Saccomanno |
| 2004/0114869 | A1 | 6/2004 | Fike et al. |
| 2005/0047705 | A1 | 3/2005 | Domash et al. |
| 2008/0004525 | A1 | 1/2008 | Goldman et al. |
| 2008/0027317 | A1 | 1/2008 | Wood et al. |
| 2008/0193080 | A1 | 8/2008 | Cheben et al. |
| 2009/0079941 | A1 | 3/2009 | Miller et al. |
| 2009/0252456 | A1 | 10/2009 | Rasras |
| 2010/0053591 | A1 | 3/2010 | Gibson et al. |
| 2011/0182549 | A1 | 7/2011 | Okayama et al. |
| 2012/0068609 | A1 | 3/2012 | Ide et al. |

FOREIGN PATENT DOCUMENTS

| | | |
|---|---|---|
| WO | 03065088 A2 | 8/2003 |
| WO | 2009106140 A1 | 9/2009 |

OTHER PUBLICATIONS

Shani et al, "Polarization rotation in asymmetric peiodic loaded rib waveguides", "Applied Physics Letters", Sep. 9, 1991, pp. 1278-1280, vol. 59, No. 11, Publisher: American Institute of Physics, Published in: US.

Davids et al., "Surface plasmon induced polarization rotation and optical vorticity in a single mode waveguide", "Optics Express", Jul. 23, 2007, pp. 9476-9485, vol. 15, No. 15, Publisher: Optical Society of America, Published in: US.

Senichi Suzuki, et al., "High-Density Integrated Planar Lightwave Circuits Using SiO2-GeO2 Waveguides with a High Refractive Index Difference", "Journal of Lightwave Technology", May 1, 1994, pp. 790-796, vol. 12, No. 5, Publisher: IEEE Service Center, New York, NY, US // ISSN: 0733-8724, DOI: 10.1109/50.293970, Published in: US.

"Related European Patent Application No. 12 180 268.0/1553", "Examination Report", Jan. 6, 2014, Publisher: EPO, Published in: EP.

Alexander Menck, "Related EP Application No. EP 12180268", "Extended Search Report", Dec. 21, 2012, Publisher: EPO, Published in: EP.

"Related U.S. Appl. No. 13/208,806", "Office Action", Oct. 8, 2014, Publisher: USPTO.

"Related U.S. Appl. No. 13/208,806", "Office Action", May 28, 2014, Publisher: USPTO, Published in: US.

"Related U.S. Appl. No. 13/208,806", "Office Action", Jul. 19, 2013, Publisher: USPTO, Published in: US.

Hung Q. Lam, "Related U.S. Appl. No. 13/208,806", "Office Action", Oct. 7, 2013, Publisher: USPTO, Published in: US.

"Related U.S. Appl. 13/289,422", "Office Action", Dec. 27, 2013, Publisher: USPTO, Published in: US.

"Related U.S. Appl. No. 13/289,422", "Office Action", Oct. 3, 2013, Publisher: USPTO, Published in: US.

"Related U.S. Appl. No. 13/289,422", "Office Action", Jun. 20, 2014, Publisher: USPTO, Published in: US.

"Related U.S. Appl. No. 14/479,665", "Non-Final Office Action", Oct. 7, 2014, Publisher: USPTO, Published in: US.

"Related U.S. Appl. No. 14/479,665", "Office Action ", Mar. 4, 2015, Publisher: USPTO, Published in: US.

Examination Report, dated Feb. 4, 2016, issued in counterpart European Patent Application No. 12180268.0.

"Final Office Action" dated Nov. 9, 2015, issued in related U.S. Appl. No. 14/491,249.

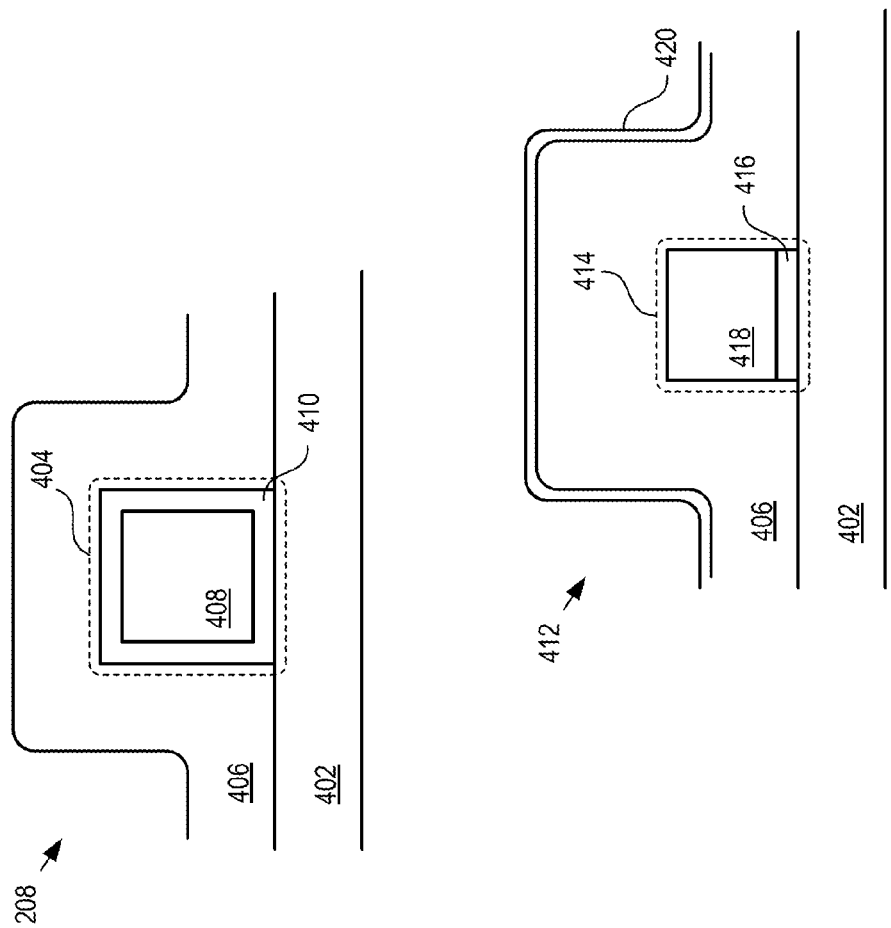

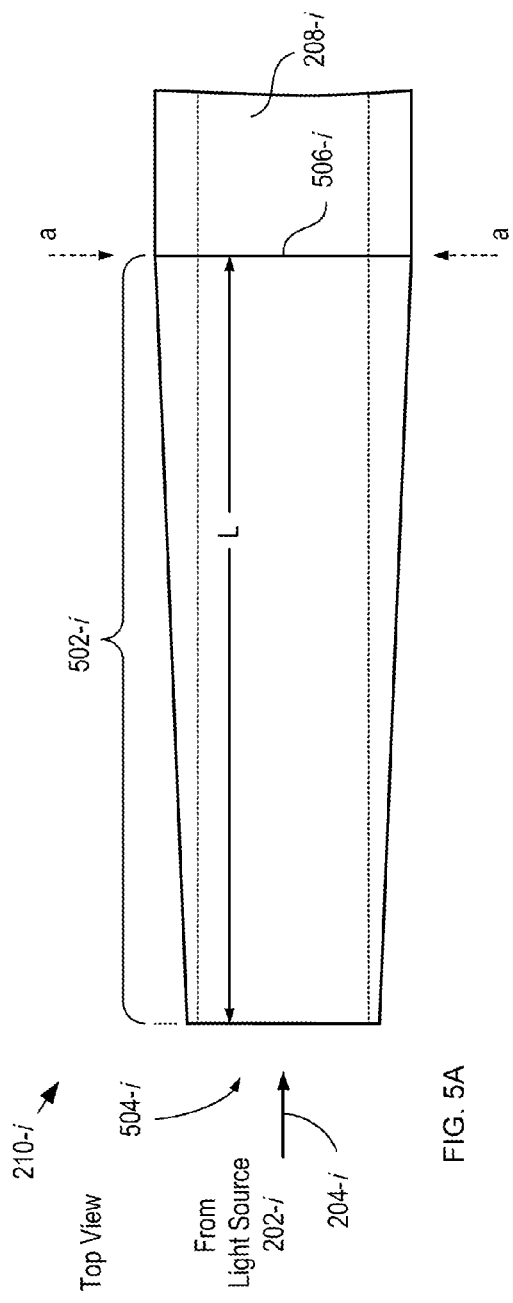
FIG. 5A
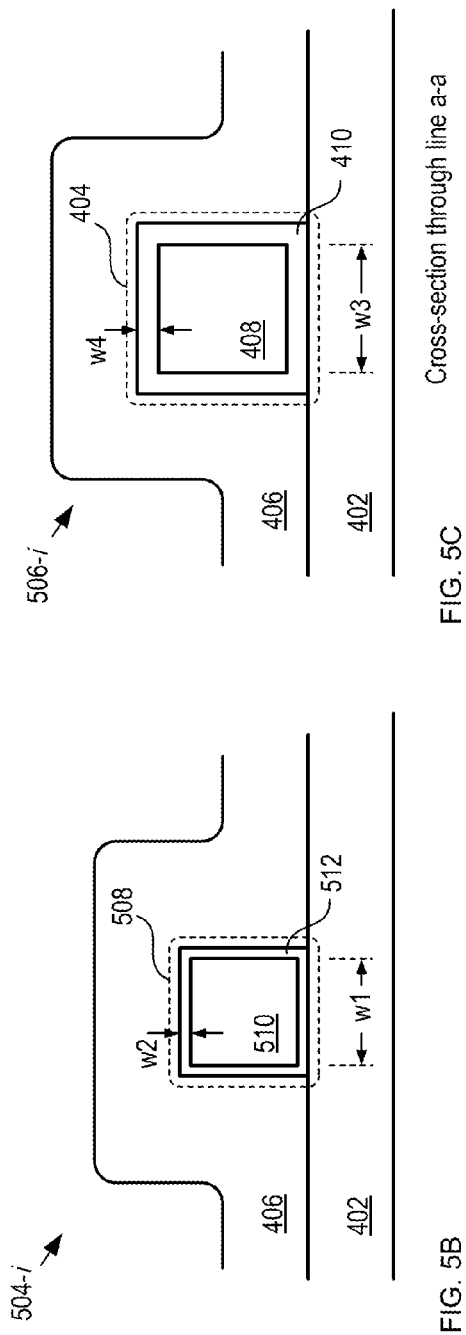
FIG. 5B
FIG. 5C

SCANNING LASER PROJECTOR

CROSS REFERENCE TO RELATED APPLICATIONS

This case is a continuation-in-part of co-pending U.S. patent application Ser. No. 13/208,806, entitled "Beam Combiner," filed Aug. 12, 2011, which claims the benefit of European Patent Application EP10008424.3, filed Aug. 12, 2010, U.S. Provisional Application Ser. No. 61/344,553, filed Aug. 19, 2010, U.S. Provisional Application Ser. No. 61/376,483, filed Aug. 24, 2010, and U.S. Provisional Application Ser. No. 61/477,960, filed Apr. 21, 2011. All of these cases are incorporated herein by reference If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to projectors in general, and, more particularly, to multi-wavelength laser projectors.

BACKGROUND OF THE INVENTION

The popularity of mobile digital devices, such as smart phones, personal data assistants, digital cameras, etc., has increased dramatically in recent years. As a result, a typical device user routinely carries vast amounts of digital information in their pockets. In addition, access to the Internet is rapidly becoming ubiquitous, increasing the amount of information at a user's fingertips dramatically. Much of this information is in the form of media, such as web pages, videos, live television, photographs, books, and the like, which is meant for display. Unfortunately, the small form-factor of many mobile digital devices, while enabling easy mobility, does not lend itself well to the display of the stored information. As a result, portable projectors (often referred to as "pico-projectors") that attach to the mobile devices and project the information onto a convenient surface have become increasingly attractive. Pico-projectors have found use in many applications, including heads-up displays in cars and planes, business presentations, and entertainment.

One popular type of projector is based on the projection of laser light. Such projectors are enabled, in part, by the development of miniature solid-state lasers. In order to project color images, light signals from multiple lasers (typically emitting red, green, and blue light) are combined using free-space optics to form a composite light beam that is then scanned over the intended display region. Unfortunately, widespread adoption of such projectors remains slow due to their relatively large size.

Another available projector type is based on liquid crystals (LC's). LC-based projectors either project an image through a liquid-crystal display, or construct the image by reflection onto a liquid-crystal-on-silicon (LCoS) display using light bulbs or LEDs as light sources.

Unfortunately, currently available pico-projectors are still relatively large, complex, and expensive. Further, projectors based on free-space optical systems require labor-intensive assembly. As a result, it is difficult to manufacture such projectors in high volume at low cost.

SUMMARY OF THE INVENTION

The present invention enables a compact laser-beam projector that overcomes some of the costs and disadvantages of the prior art. Embodiments of the present invention are particularly well suited for use in applications such as entertainment, medical diagnostics, cancer treatment, insect control, thermal hot spot mapping for integrated circuits or printed-circuit boards, and virtual keyboards.

The present invention provides a platform for combining a plurality of light signals of different wavelengths into a single output beam that can be scanned to render an image on a surface. Embodiments of the present invention are based on planar lightwave circuit-based beam combiners that can combine a plurality of light signals of disparate wavelengths over a wide wavelength range. The beam combiner comprises planar lightwave circuit having a plurality of input ports, a mixing region, and an output port, wherein the mixing region includes a plurality of directional couplers that are arranged in a tree structure. The planar lightwave circuits are based on single-mode surface waveguides having a core comprising stoichiometric silicon nitride and cladding of stoichiometric silicon dioxide.

Beam combiners in accordance with the present invention enable low-cost, automated assembly, hybrid integration of the beam combiners and light sources that provide the constituent light signals. Embodiments of the present invention, therefore, can be less expensive and/or smaller than laser projectors of the prior art. Further, planar lightwave circuit-based beam combiners can be more robust and less sensitive to shock and vibration than free-space beam combiners, resulting in laser projectors that are more robust than typical prior-art laser projectors.

In some embodiments, at least one input port has a mode-matching region that enables direct, low-loss optical coupling of the output facet of a laser diode to the beam combiner. The mode-matching region includes a waveguide region that is tapered from an end facet to an interface so that the effective refractive-index contrast at the end facet is lower or higher than the effective refractive-index contrast at the interface. At the interface, the optical mode is mode-matched to the waveguide structure that forms the bulk of the planar lightwave circuit.

In some embodiments, the beam combiner comprises waveguide-based attenuators for controlling the intensity one or more of the light signals combined in the composite output signal.

In some embodiments, reflected light from each image point in the image region is used to determine one or more measurands of that image point. At least one light signal in the output beam is selected so that the measurand induces a detectable difference in its reflected light. In some embodiments, when a difference in the reflected light is detected, one or more additional light signals of different wavelengths are added to the output beam and are simultaneously projected onto the surface.

An embodiment of the present invention is a projector for forming a real-time image of the vein structure in a region of a patient's body on the surface of the skin. The illustrative embodiment comprises a first light source that emits a light signal of a first wavelength that is readily absorbed by the blood carried in the veins. This light signal is collimated to form an output beam that is scanned over a region of the skin, which reflects a portion of the output beam to a photodetector. When an image point comprises a portion of a vein, the intensity of the reflected light decreases, thereby indicating the presence of the vein. In response to a decrease in the reflected signal, the projector adds a second light signal of a second wavelength to the output beam, wherein the second wavelength is readily visible to a user—thereby enhancing visibility of that image point to the user. The projector scans the entire region at a rate sufficient to generate a real-time image of the sub-surface vein structure on the skin.

An embodiment of the present invention is a scanning projector comprising: a first light source that provides a first light signal characterized by a first wavelength; a second light source that provides a second light signal characterized by a second wavelength; a beam combiner comprising a planar lightwave circuit including a plurality of waveguides that are arranged to define a first input port, a second input port, a mixing region, and an output port, the beam combiner: (1) receiving the first light signal at the first input port, (2) receiving the second light signal at the second input port, (3) combining the first light signal and the second light signal into a composite output signal, and (4) providing the composite output signal at the output port; and a scanner, the scanner receiving the composite output signal from the beam combiner and scanning the composite output signal over each of a plurality of image points in a first region.

BRIEF DESCRIPTION OF THE DRAWINGS

FIG. 4A depicts a schematic drawing of a cross-sectional view of a waveguide in accordance with the illustrative embodiment of the present invention.

FIG. 4B depicts a schematic drawing of a cross-sectional view of a waveguide in accordance with a first alternative embodiment of the present invention.

FIG. 5A depicts a schematic drawing of a top view of an input port comprising a mode-matching region in accordance with the illustrative embodiment of the present invention.

FIG. 5B depicts a schematic drawing of a cross-sectional view of end facet 504-$i$.

FIG. 5C depicts a schematic drawing of a cross-sectional view of interface 506-$i$.

DETAILED DESCRIPTION

Figure 1:
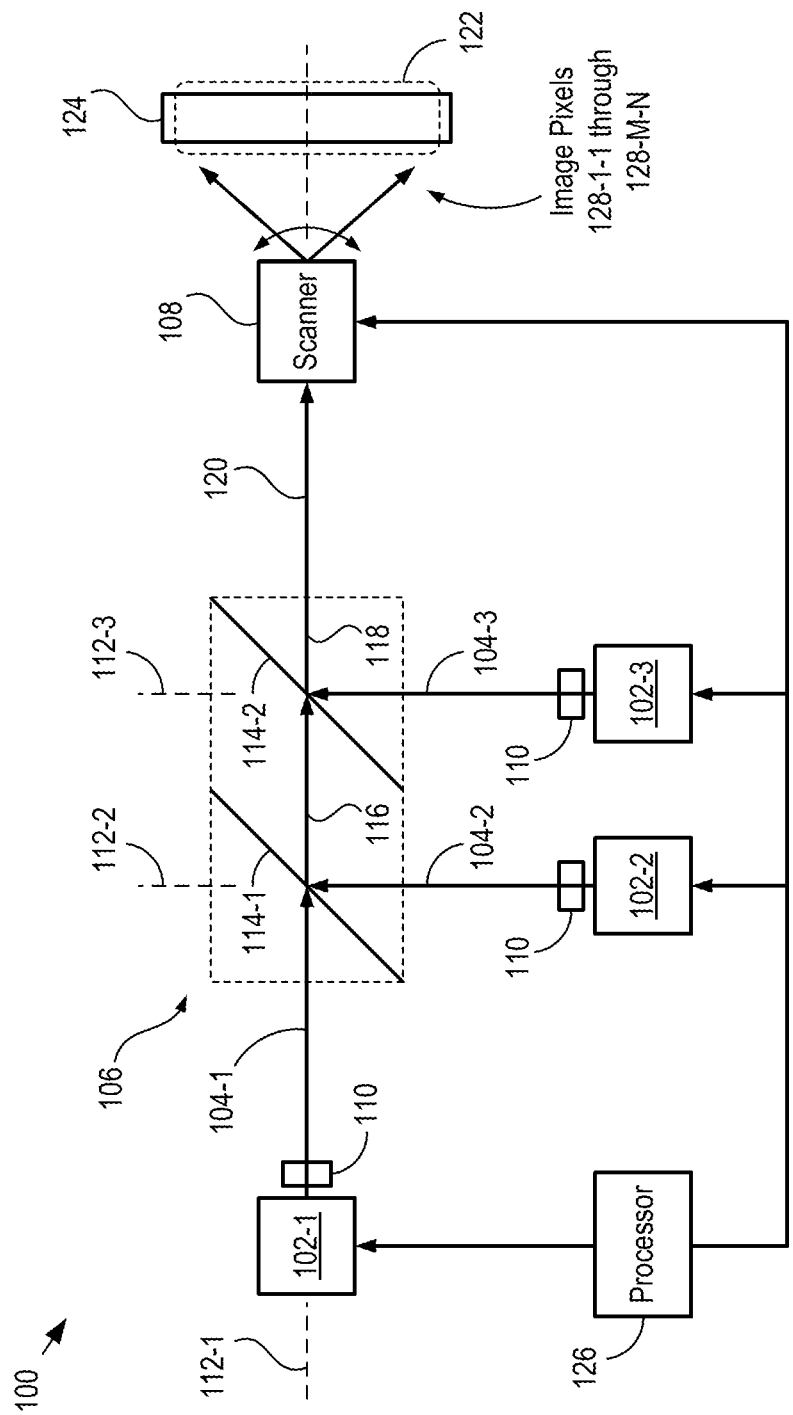
FIG. 1 depicts a schematic drawing of a scanning laser projector in accordance with the prior art.

FIG. 1 depicts a schematic drawing of a scanning laser projector in accordance with the prior art. Projector 100 comprises light sources 102-1 through 102-3, beam combiner 106, scanner 108, and processor 126. Examples of conventional scanning laser projectors can be found in, for example, U.S. Pat. No. 7,978,189, issued Jul. 12, 2011, which is incorporated herein by reference.

Light sources 102-1 through 102-3 are laser diodes that provide narrow spectral-width light signals 104-1 through 104-3, respectively (referred to, collectively, as light signals 104). Light source 102-1 provides light signal 104-1, which is a light signal of a wavelength in the blue light region (e.g., 445 nm). Light source 102-2 provides light signal 104-2, which is a light signal of a wavelength in the green light region (e.g., 532 nm). Light source 102-3 provides light signal 104-3, which is a light signal of a wavelength in the red light region (e.g., 640 nm). Each of light sources 102-1 through 102-3 includes beam-shaping optic 110 that shapes each of light signals 104-1 through 104-3 into substantially collimated beams and directs them along axes 112-1, 112-2, and 112-3, respectively.

Beam combiner 106 comprises selective fold mirrors 114-1 and 114-2. Selective fold mirror 114-1 is a dichroic mirror that is transparent for light signal 104-1 but substantially reflects light signal 104-2. Selective fold mirror 114-1 is aligned at an angle of 45° with respect to each of axes 110-1 and 110-2.

Selective fold mirror 114-2 is a dichroic mirror that is transparent for light signals 104-1 and 104-2 but reflects light signal 104-3. Selective fold mirror 114-2 is aligned at an angle of 45° with respect to each of axes 110-1 and 110-3. Typically, light sources 102, beam-shaping optics 110, and mirrors 114-1 and 110-2 are mounted in a rigid fixture, such as an optical sub-mount, which keeps them in their relative positions.

In operation, beam combiner 106 receives each of light signals 104-1 and 104-2 such that the light signals are coincident at the center of selective fold mirror 114-1. Selective fold mirror 114-1 allows light signal 104-1 to pass through and continue along axis 110-1 but turns light signal 104-2 from axis 110-2 to axis 110, where it combines with light signal 104-1 to form dual-wavelength light signal 116.

In similar fashion, beam combiner 106 receives light signal 104-3 such that it is coincident with light signal 116 at the center of selective fold mirror 114-2. Selective fold mirror 114-2 allows light signal 116 to pass through and continue along axis 110-1 but turns light signal 104-3 from axis 110-3 to optical axis 110-1, where it combines with light signal 116 to collectively define composite output signal 118. Composite output signal 118 exits beam combiner 106 as a collimated free-space beam 120.

Scanner 108 receives beam 120 and steers it about a two-dimensional cone to render an image on image region 122 of surface 124. Scanner 108 is a conventional scanner, such as a two-axis gimbal-mounted MEMS mirror, a galvo scanner, and the like. Processor 126 controls the angular position of scanner 108 and, therefore, the position of beam 120 in image region 122.

Processor 126 is typically a conventional digital video processor suitable for interfacing with a video source (e.g., cell phone, PDA, etc.), modulating light sources 102-1 through 102-3 to control the relative intensities of light signals 104-1 through 104-3, and controlling scanner 108 so that it traces beam 120 appropriately across image region 122.

Processor 126 normally comprises a video controller that receives an input video signal from the video source and buffers the received video images in memory. To display a video frame, the controller reads the a stored video frame from the memory and drives light sources 102 so that they emit their respective light signals at the appropriate intensity for generating the desired color and brightness at each image pixel 128 as beam 120 is scanned across image region 122.

Projectors based on free-space beam combiners, such as beam combiner 106, are beset by several drawbacks, however. First, free-space beam combiners require optical elements that are relatively large and bulky, which results in a projector that is also relatively large and bulky. Typically, scanning laser projectors are intended for use with that is roughly pocketsize. A reliance on free-space beam combiners has resulted in conventional laser projectors that are much larger than the video sources, however. As a result, the relatively large size of conventional scanning projectors has, thus far, limited their widespread adoption.

Second, free-space beam combiners convey light through a medium (e.g., air, glass, etc.) that provides no light-guiding capability. As a result, it is necessary to include beam-shaping optics, such as a collimator, for shaping each constituent light signal prior to its receipt by the beam combiner to ensure that each beam has substantially the same cross-sectional shape when combined. The need for beam-shaping optics adds significant system cost and complexity.

Third, the assembly of the optical elements of a free-space beam combiner is typically highly labor intensive. These optical elements must be carefully aligned in both position and angle to ensure that the constituent light signals are completely overlapping to avoid spectral non-uniformity through the cross-section of the composite output beam. In addition, angular misalignment of one or more of constituent light signals can lead to divergence of those light signals as they propagate through the beam combiner. The assembly of these optical elements becomes increasingly more difficult as additional light signals are included. Further, high-speed volume manufacture of free-space beam combiners is difficult in a cost-effective manner. Still further, the sources, mirrors, and lenses are normally aligned and positioned by mounting them in an optical fixture. Unfortunately, such fixtures are susceptible to temperature-induced misalignments (due to thermal expansion), as well as misalignments caused by shock and vibration that commonly occur through the lifetime of the projector.

Fourth, geometric distortion of the constituent light signals (e.g., light signals 102-2 and 102-3) occurs at each turning mirror due to the difference in the angle of incidence in the x- and y-directions between the beams and the mirrors (e.g., mirrors 114-1 and 114-2). As a result, it is often necessary to include beam-shape compensation optics, which further increases cost, complexity, and system size.

Fifth, conventional laser projectors rely on direct modulation of the laser sources to control the color of the composite output signal. Unfortunately, changing the drive current to a laser diode can lead to deleterious optical effects, such as wavelength chirping and mode hopping, that manifest as unwanted visible artifacts in the projected image. In addition, some laser sources, such as frequency-doubled lasers or diode-pumped solid-state lasers, cannot be controlled using direct current drive modulation and, therefore, rely upon external modulators, such as acousto-optic modulators, to control their output. External modulation adds significant complexity and expense to such systems.

In contrast to projectors of the prior art, laser projectors in accordance with the present invention employ beam combiners based on planar lightwave circuits (PLCs). For the purposes of this Specification, including the appended claims, a "planar lightwave circuit" is defined as an optical circuit that comprises one or more monolithically integrated surface waveguide structures that guide light in two dimensions, wherein the surface waveguides are arranged to provide at least one optical function. Beam combiners in accordance with the present invention comprise "high-contrast" surface waveguides whose cores comprise silicon nitride. Further, beam combiners in accordance with the present invention enable a single composite light signal to be formed by combining light signals of disparate, irregularly spaced wavelengths over a wide wavelength range.

It should be noted that PLC-based devices exist in the prior art that can be used to combine two or more light signals of different wavelengths—namely, array waveguide gratings (AWGs). An AWG, however, requires that the wavelengths being combined be closely spaced and be regularly spaced. As a result, an AWG does not have the diversity and flexibility required for laser projector applications.

Figure 2:
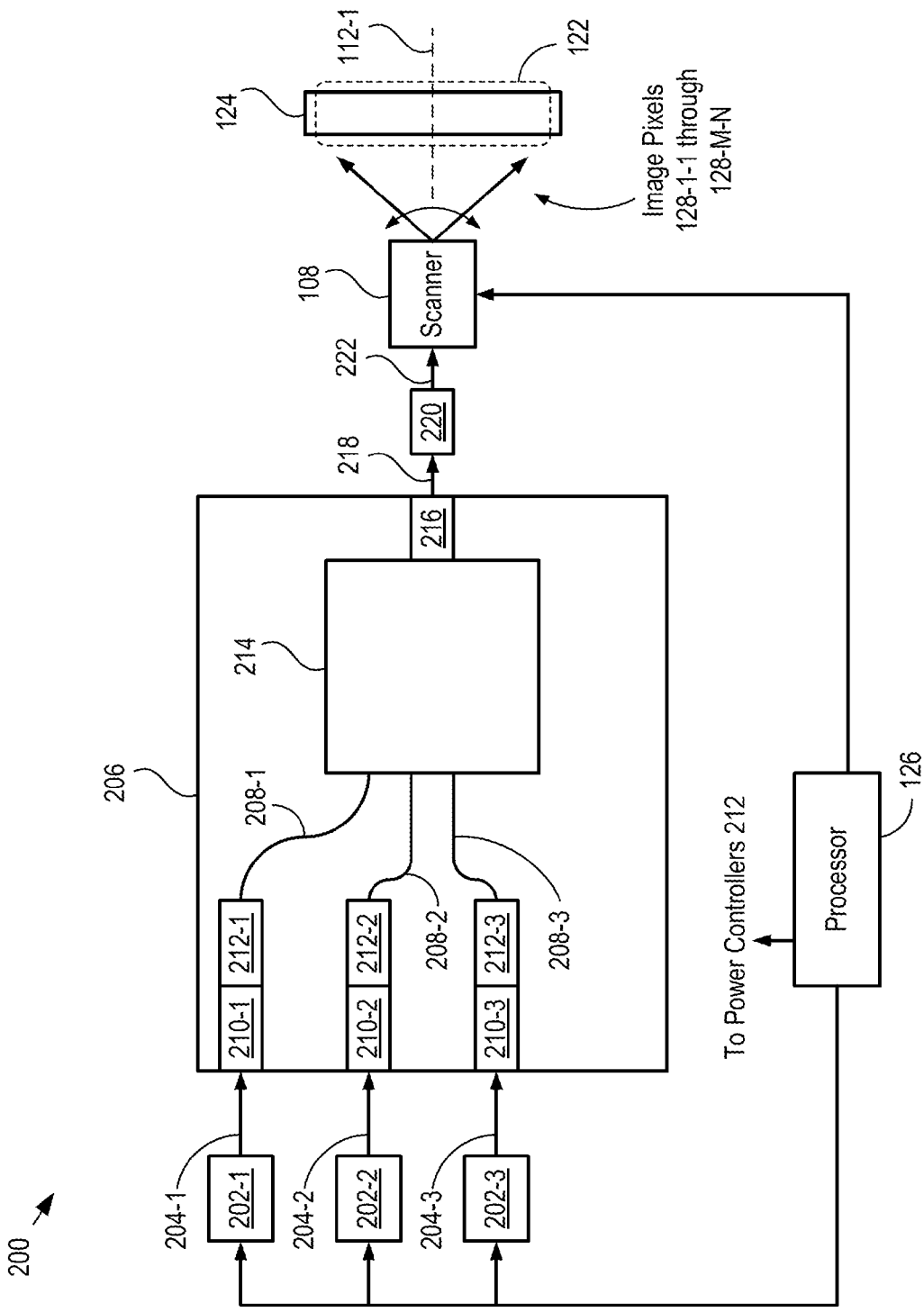
FIG. 2 depicts a schematic drawing of a scanning projector in accordance with an illustrative embodiment of the present invention.

FIG. 2 depicts a schematic drawing of a scanning projector in accordance with an illustrative embodiment of the present invention. Projector 200 comprises light sources 202-1 through 202-3, beam combiner 206, lens 220, scanner 108, and processor 126. Projector 200 projects a full-color image in the visible light range.

Figure 3:
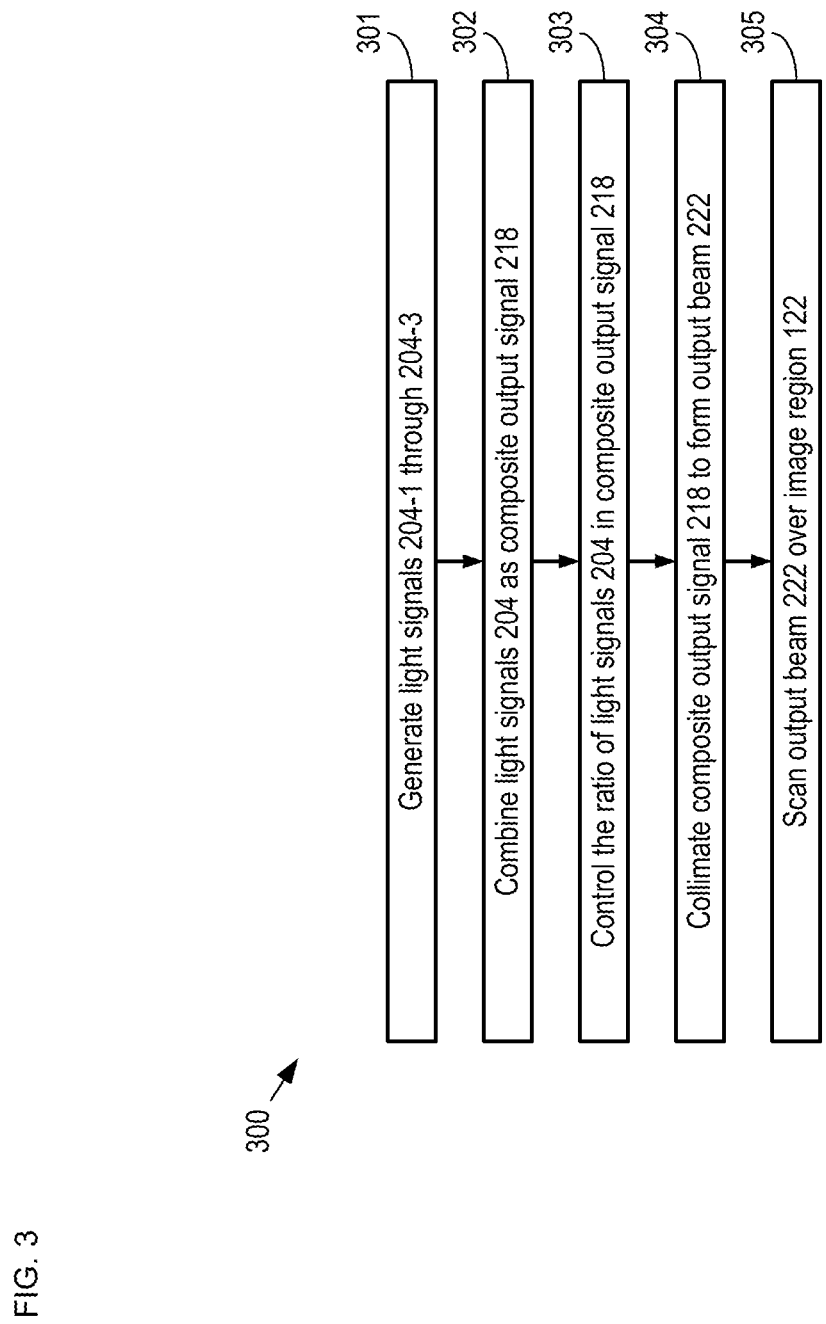
FIG. 3 depicts operations of a method for projecting an image in accordance with the illustrative embodiment of the present invention.

FIG. 3 depicts operations of a method for projecting an image in accordance with the illustrative embodiment of the present invention. Method 300 begins with operation 301, wherein light signals 204-1 through 204-3 (referred to, collectively, as light signals 204) are generated by light sources 202-1 through 202-3 (referred to, collectively, as light sources 202). Method 300 is described with continuing reference to FIG. 2 and reference to FIGS. 4-7.

Light sources 202-1 through 202-3 are laser diodes that provide narrow spectral-width light signals 204-1 through 204-3, respectively (referred to, collectively, as light signals 204). Light source 202-1 provides light signal 204-1, which is a light signal of a wavelength in the blue region (e.g., 445 nm). Light source 202-2 provides light signal 204-2, which is a light signal of a wavelength in the green light region (e.g., 532 nm). Light source 202-3 provides light signal 204-3, which is a light signal of a wavelength in the red light region (e.g., 640 nm). In some embodiments, light signals 204 are characterized by different wavelengths within the visible light region. In some embodiments, at least one of light signals 204 is characterized by a wavelength that is outside of the visible light region, such as the ultraviolet region, near-infrared region, or mid-infrared region.

At operation 302, light signals 204 are combined at beam combiner 206 to form composite output signal 218.

Beam combiner 206 is a PLC-based beam combiner that comprises waveguides 208-1 through 208-3, input ports 210-1 through 210-3, power controllers 212-1 through 212-3, mixing region 214, and output port 216.

Each of waveguides 208-1 through 208-3 (referred to, collectively, as waveguides 208) is a single-mode waveguide characterized by a large difference between the refractive index of its core material and cladding material (typically referred to as "a high-contrast waveguide"). As a result, each of waveguides 208 is characterized by strong optical mode confinement, can include curved sections that have small bend radii, and can include waveguides in a densely packed arrangement. Planar lightwave circuits based on waveguide 208, therefore, can provide a high degree of functionality in a much smaller footprint than conventional low-index waveguide-based planar lightwave circuits.

FIG. 4A depicts a schematic drawing of a cross-sectional view of a waveguide in accordance with the illustrative embodiment of the present invention. Waveguide 208 is a composite-core waveguide (referred to, herein, as a TriPleX™ waveguide), such as is described in U.S. Pat. No. 7,146,087, issued Dec. 5, 2006, which is incorporated herein by reference. Waveguide 208 comprises lower cladding 402, core 404, and upper cladding 406. Waveguide 208 is representative of each of waveguides 208-1 through 208-3.

Waveguide 208 is based on a material system of silicon nitride and silicon dioxide. Such a waveguide can be designed for operation at any wavelength from the ultraviolet range to the mid-infrared range. As a result, beam combiner 206 enables projector 200 to project light beams of a diversity of irregularly or regularly spaced wavelengths. One skilled in the art will recognize that conventional silica-based PLC technology is not well suited to applications wherein multiple light signals characterized by disparate wavelengths over a wide wavelength range must be combined.

Lower cladding 402 is a layer of silicon dioxide having a thickness typically within the range of approximately 1 micron to approximately 10 microns. Lower cladding 402 can be formed by any of a number of conventional methods, including thermal growth, LPCVD deposition, spin-on coating, and the like. It will be clear to one skilled in the art how to specify, make, and use lower cladding 402.

Core 404 comprises inner core 408 and outer core 410, which completely surrounds inner core 408.

Inner core 408 comprises stoichiometric silicon dioxide. Inner core 408 has a substantially square cross-sectional shape having a size, w1, of approximately 1 micron on a side. In some embodiments, inner core 408 has a different shape and/or different dimensions.

Outer core 410 comprises stoichiometric silicon nitride having a thickness equal to w2. In the illustrative embodiment, w2 is approximately equal to 200 nm; however, it will be clear to one skilled in the art, after reading this Specification, how to specify, make, and use alternative embodiments of the present invention wherein w2 is any practical size.

In some embodiments, outer core 410 does not completely surround inner core 410. In some embodiments, outer core 410 comprises a layer of stoichiometric silicon nitride disposed on inner core 408 and/or a layer of stoichiometric silicon nitride that interposes inner core 408 and lower cladding 402.

Upper cladding 406 is a layer of silicon dioxide formed as a conformal coating over core 404. Upper cladding 406 is formed using conventional conformal deposition techniques, such as plasma-enhanced chemical vapor deposition, low-pressure chemical vapor deposition using tetraethyl orthosilicate (TEOS) as a precursor gas, and the like.

FIG. 4B depicts a schematic drawing of a cross-sectional view of a waveguide in accordance with a first alternative embodiment of the present invention. Waveguide 412 is a silicon-nitride-core waveguide that comprises lower cladding 402, core 414, upper cladding 406, and barrier layer 420.

Core 414 comprises lower core 416 and upper core 418, which is disposed on lower core 416.

Lower core 416 comprises stoichiometric silicon nitride. Lower core 416 has a substantially rectangular cross-sectional shape having a width within the range of approximately 0.8 microns to approximately 3 microns and a height within the range of approximately 3 nm to approximately 30 nm. In some embodiments, lower core 416 has a different shape and/or different dimensions.

Upper core 418 comprises silicon dioxide deposited using TEOS as a precursor gas. Upper core 418 has a width substantially equal to the width of lower core 416 and a thickness within the range of approximately three to approximately twenty times the thickness of lower core 416. In some embodiments, upper core 418 enables a reduction in the internal stress of lower core 416 and/or reduces scattering in lower core 416, as well as having other positive effects that lead to a reduction in propagation loss for light propagating through waveguide 412. One skilled in the art will recognize, after reading this Specification, that the dimensions of lower core 416 and/or upper core 418 are based on several factors, including the wavelength of light that is expected to propagate through the waveguide.

Upper cladding 406 is covered with optional barrier layer 420. Barrier layer 420 comprises silicon nitride and provides a barrier to moisture and contaminants that might otherwise be absorbed by waveguide 412. In some embodiments, barrier layer 420 is not included.

One skilled in the art will recognize, after reading this Specification, that the waveguide structures depicted in FIGS. 4A and 4B represent only two examples of waveguide structures suitable for use in beam combiner 206. It will be clear to one skilled in the art, after reading this Specification, that waveguide structures suitable for use in beam combiner 206 include, without limitation, ridge waveguides, channel waveguides, stripe waveguides, multi-layered waveguides, femto-second laser-written waveguides, graded-index waveguides, and the like.

At its input, each of waveguides 208 comprises an input port that comprises a mode-matching region, which enables the waveguide to optically couple light directly from the output facet of its corresponding light source 202 without large coupling losses. Specifically, waveguide 208-1 comprises input port 210-1, which enables low-loss optical coupling with light source 202-1, waveguide 208-2 comprises input port 210-2, which enables low-loss optical coupling with light source 202-2, and waveguide 208-3 comprises input port 210-3, which enables low-loss optical coupling with light source 202-3.

FIG. 5A depicts a schematic drawing of a top view of an input port comprising a mode-matching region in accordance with the illustrative embodiment of the present invention. Input port 210-$i$ is representative of each of input ports 210-1 through 210-3.

Mode-matching region 502-$i$ is a region of waveguide 208-$i$ whose cross-sectional area is gently tapered such that it increases monotonically from end facet 504-$i$ to interface 506-$i$ along length L. Mode-matching region 402-$i$, therefore, gently transitions from (1) an effective index-contrast that yields a mode-field diameter at end facet 504-$i$ that substantially matches the mode-field diameter of the light source to (2) an effective index-contrast that yields a mode-field diameter at interface 506-$i$ that substantially matches the mode-field diameter of waveguide 208-$i$. As a result, the optical mode of light propagating through mode-matching region 402-$i$ is matched to the optical mode of the output facet of light source 202-$i$ at end facet 504-$i$, while the optical mode of light propagating through mode-matching region 402-$i$ is matched to the optical mode of waveguide 208-$i$ at interface 506-$i$.

FIG. 5B depicts a schematic drawing of a cross-sectional view of end facet 504-$i$. End facet 504-$i$ comprises lower cladding 402, inner core 510, outer core 512, and upper cladding 406.

Inner core 510 is analogous to inner core 408; however, inner core 510 has a substantially square cross-sectional shape having a size of w1, where w1 is smaller than the size of inner core 408 (1 micron in the illustrative embodiment).

Outer core 512 is analogous to outer core 410; however, outer core 512 has a thickness of w2, where w2 is smaller than the thickness of outer core 410 (200 nm in the illustrative embodiment).

FIG. 5C depicts a schematic drawing of a cross-sectional view of interface 506-$i$. Interface 506-$i$ comprises lower cladding 402, inner core 408, outer core 410, and upper cladding 406. In other words, interface 506-*i* has the same dimensions and layer structure as waveguide 208. As a result, light propagating through mode-matching region 503-*i* experiences substantially lossless (i.e., adiabatic) transition into waveguide 208.

It should be noted that, in some embodiments, the inclusion of mode-matching regions in the input ports of a beam combiner mitigates many of the assembly issues that impact prior-art projectors by enabling light sources 202 to be easily integrated with beam combiner 206 by mounting the laser diodes directly on the beam combiner substrate itself. This enables each light signal output at the output facets of the laser diodes to be directly coupled into its corresponding input port 210. As a result, the integrated light sources and beam combiner collectively define a substantially solid "light engine" that is more robust and can be significantly more compact than possible with prior-art approaches.

In some embodiments, however, light sources 202 are not directly integrated with beam combiner 206. In some embodiments, light sources 202 are fiber-coupled laser diodes that provide light signals 204 to beam combiner 206 via optical fiber pigtails that are attached directly to appropriately mode-matched input ports of a beam combiner.

One skilled in the art will recognize, after reading this specification, that since waveguides 208 provide waveguiding in two dimensions, light signals 204 need not be collimated prior to their coupling into the beam combiner. This eliminates the need for beam-shaping optics at each light source. It also mitigates the effects of angular misalignment, since spectral non-uniformity through the cross-section of the composite output beam and beam divergence issues are eliminated. Further, the elimination of the beam-shaping optics and the integration of the light sources and beam combiner enable a significant reduction in the overall size of the optical system. In fact, in some embodiments, the size of the optical system is small enough to enable a pen-sized projector 200, or enable projector 200 to be integrated directly into a mobile digital device, such as a cell phone or personal digital assistant (PDA).

Figure 6:
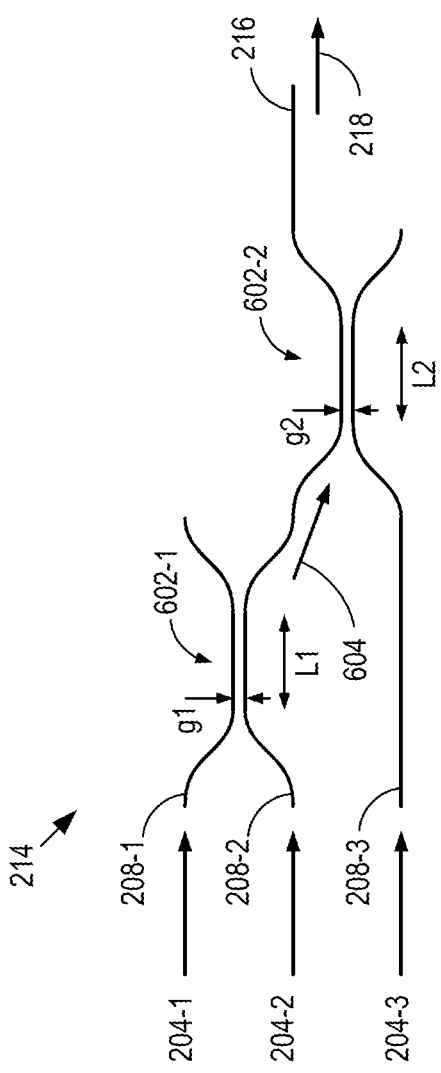
FIG. 6 depicts a schematic drawing of mixing region 214.

FIG. 6 depicts a schematic drawing of mixing region 214. Mixing region 214 comprises portions of waveguides 208-1 through 208-3, which have been arranged to form directional couplers 602-1 and 602-2.

Directional coupler 602-1 comprises first portions of waveguides 208-1 and 208-2, which are separated by gap g1 along interaction length L1. Directional coupler 602-1 is a symmetric coupler (i.e., the portions of waveguides 208-1 and 208-2 have substantially the same width) that is characterized by wavelength-dependent power coupling that varies slowly with wavelength. The values of g1 and L1 are carefully chosen to enable substantially all of the optical energy in light signal 204-1 to optically couple from waveguide 208-1 into waveguide 208-2 along interaction length L1, but substantially none of the optical energy in light signal 204-2 optically couples from waveguide 208-2 to waveguide 208-1. As a result, directional coupler 602-1 provides both light signals 204-1 and 204-2, combined as dual-wavelength signal 604, on waveguide 208-2.

Directional coupler 602-2 comprises a second portion of waveguide 208-2 and a portion of 208-3, which are separated by gap g2 along interaction length L2. Directional coupler 602-2 is also a symmetric coupler that is characterized by wavelength-dependent power coupling that varies slowly with wavelength. The values of g2 and L2 are carefully chosen to enable substantially all of the optical energy in light signal 204-3 to optically couple from waveguide 208-3 into waveguide 208-2 along interaction length L2, but substantially none of the optical energy in light signal 604 optically couples from waveguide 208-2 to waveguide 208-3. As a result, directional coupler 602-2 provides all three of light signals 204-1 through 204-3, combined as composite output signal 218, on waveguide 208-2.

Although the illustrative embodiment comprises a beam combiner having three waveguides and three input ports, it will be clear to one skilled in the art, after reading this Specification, how to specify, make, and use alternative embodiments that comprise beam combiners having any practical number of waveguides and input ports. As discussed in U.S. patent application Ser. No. 13/208,806, beam combiners in accordance with the present invention can include additional branches or hierarchy stages that enable the addition of additional light signals to the system. The ability to readily include more waveguides and ports enables, for example, the inclusion of redundant light sources for each light signal without significantly increasing the overall size of projector 200.

At operation 303, processor 126 controls the ratio of optical power from light signals 204 in composite output signal 218 via power controllers 212-1 through 212-3.

Figure 7:
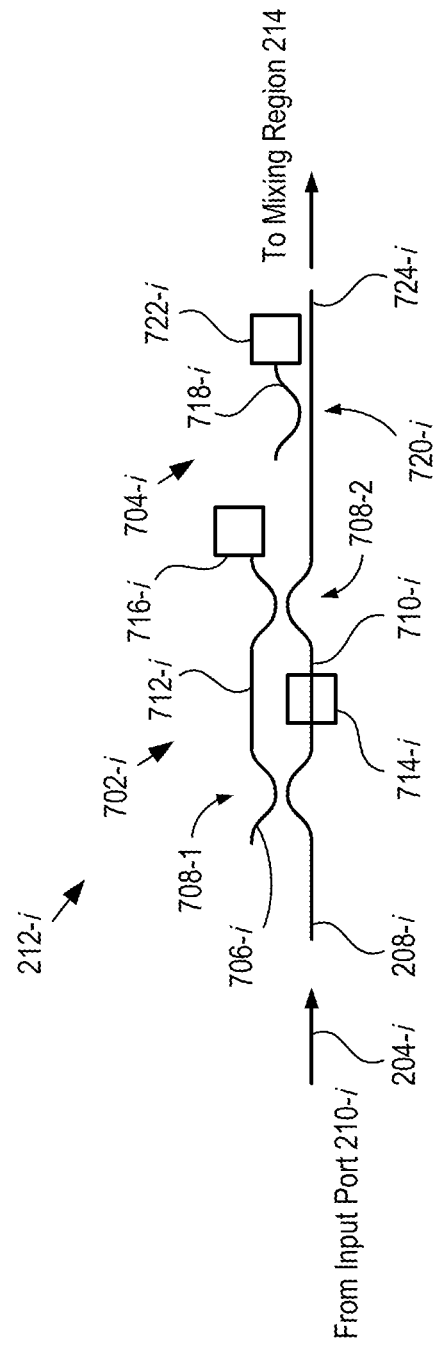
FIG. 7 depicts a schematic drawing of a power controller in accordance with the illustrative embodiment of the present invention.

FIG. 7 depicts a schematic drawing of a power controller in accordance with the illustrative embodiment of the present invention. Controller 212-*i* comprises attenuator 702-*i* and power monitor 704-*i*. In response to control signals from processor 126 (not shown for clarity) and the output of power monitor 704-*i*, controller 212-*i* diverts optical power (via attenuator 702-*i*) from waveguide 208-*i* to a light dump in order to control the amount of optical power of light signal 204-*i* that reaches mixing region 214.

Attenuator 702-*i* comprises waveguide 208-*i* and waveguide 708-*i*, which are arranged to define directional couplers 708-1 and 708-2.

Directional couplers 708-1 and 708-2 are substantially identical directional couplers arranged in series and interposed by waveguide portions 710-*i* and 712-*i*. Waveguide portion 710-*i* is a first portion of waveguide 208-*i*. Waveguide portion 712-*i* is a waveguide having structure analogous to that of waveguide 208. Waveguide portion 712-*i* is optically coupled with light dump 716-*i*. It will be clear to one skilled in the art how to specify, make, and use light dump 716-*i*.

Modulator 714-*i* comprises a heater strip for thermally inducing a phase shift in the light that propagates through waveguide portion 710-*i*. This phase shift determines the amount of optical coupling occurs between waveguide portions 710-*i* and 712-*i*. This optical coupling, in turn, dictates how much of the optical power of light signal 204-*i* is diverted into waveguide portion 712-*i* and lost at light dump 716-*i*. The remainder of light signal 204-*i* continues propagating in waveguide 208-*i* to output 724-*i*.

Although the illustrative embodiment comprises modulators that operate on a thermo-optic effect, it will be clear to one skilled in the art, after reading this Specification, how to specify, make, and use alternative embodiments of the present invention that comprise modulators that induce a phase shift in light propagating in a waveguide based on a different effect, such as electro-optic, opto-mechanical, etc.

Power monitor 704-*i* comprises waveguide 208-*i*, waveguide 718-*i*, and photodetector 722-*i*. Waveguide 208-*i* and waveguide 718-*i* are arranged to define directional coupler 720-*i*.

Directional coupler 720-*i* enables a small percentage of its optical power to be coupled from waveguide 208-*i* into waveguide portion 718-*i*.

Waveguide portion 718-*i* is optically coupled with conventional photodetector 722-*i* (e.g., photodiode, avalanche photodiode, CCD sensor element, etc.), which is electrically coupled with controller 132 to provide the controller with a feedback signal suitable for controlling attenuator 702-*i*.

It is an aspect of the present invention that the use of power controllers 212-1 through 212-3 obviates the need to vary the drive current to each of light sources 202 to control the color of composite output signal 218. As a result, embodiments of the present invention can avoid undesirable optical effects in the composite output signal, such as wavelength chirping, accelerated degradation, mode hopping, and the like. The use of power controllers 212 also enables the use of laser sources, such as frequency doubled lasers or diode-pumped solid-state lasers, without a need for their customary external modulators. Further, since the attenuators are easily integrated in the PLC design, their inclusion adds little or no additional size to the overall system. It should be noted, however, that in some embodiments, power controllers 212 are not included and the intensity of light signals 204 is controlled conventionally by controlling the drive current to each of light sources 202.

At operation 304, composite output signal 218 is emitted into free space at output port 216. Composite output signal 218 is received by lens 220, which substantially collimates the signal to form output beam 222. Lens 220 is a conventional bulk optic lens suitable for collimating the optical emission at output port 216. In some embodiments, lens 220 is an integrated lens formed directly on the exit facet of output port 216.

At operation 305, scanner 108 receives output beam 222 and scans it over region 122 to form an image on sample 124.

It should be noted that projector 200 provides a collimated light beam that remains in focus, even when projected onto a surface that is not flat. In addition, image resolution is determined only by the spot size of output beam 222, rather than the resolution of a CCD camera, video processor, or liquid-crystal element, which enables a simpler, cheaper projection system.

The advantages afforded embodiments of the present invention enable a projector platform that is adaptable for use in many applications beyond that of simple image projection. It should be noted, therefore, that the illustrative embodiment represents only one example of a projector in accordance with the present invention. Alternative embodiments include projectors adapted for use in applications that include, without limitation, visualization and treatment of cancer tissue, pest control, insect control, visual enhancement of hot spots in semiconductor material or integrated circuits, virtual keyboards, smart targeting systems for laser-guided munitions, laser-based weapons, confocal microscopy, laser light based quality control in the medical or food industry or laser based sorting in waste and recycling processes, etc. As a result, details of the projector and the method for its use, such as the number of light signals, wavelengths selected, component arrangement, and the like, are for example only and one skilled in the art will recognize that embodiments of the present invention suited for some or all of these applications will differ from the illustrative embodiment described herein.

Vein Imaging

An application for which the present invention is particularly well suited for is the enhancement of the visibility of subcutaneous vein structure in bodily tissue. Enhanced vein visibility facilitates the performance of medical procedures by a medical practitioner, such as insertion of catheters, syringes, intravenous tubes, identification of blood clots or internal hemorrhaging, minimally invasive surgery, and the like.

Vein imaging systems are known in the prior art, such as systems described in U.S. Patent Application Publication 2008/0004525, published Jan. 3, 2008 and U.S. Patent Application Publication 2008/027317, published Jan. 31, 2008, each of which is incorporated herein by reference.

In U.S. Patent Application Publication 2008/0004525 (hereinafter referred to as the "525 application"), a scanning projector scans a first light signal over a image points in a sample region, wherein the first light signal of a wavelength that is readily absorbed by blood (i.e., 740 nm). The first light signal is reflected from the image points and detected at a photodetector. The output of the photodetector is used to create a digital map of the absorption of the first light signal in the sample region, wherein the absorption map represents the vein structure within the scanned area. Once this absorption map has been created, it is projected, using the same projection system, over the sample region using a second light signal of a wavelength visible to the eye (e.g., 630 nm).

Unfortunately, the system disclosed in the 525 application has several drawbacks. First, the absorption map is generated over the entire sample region (during a period of 60 frames of the video cycle) prior to rendering the visible image of the vein structure (also during a period of 60 frames of the video cycle). This leads to a significant delay between the projection of each successive visible image on the sample. As a result, this system is prone to errors due to practitioner hand jitter or patient motion. In addition the system is also prone to the development of image flicker, which, in addition to creating an annoyance, can also lead to more serious issues such as epileptic seizure.

In addition, the system disclosed in the 525 application employs a free-space beam combiner into which the outputs of the 740 nm and 630 nm lasers are "projected." Further, the 740 nm and 630 nm lasers are directly driven to control their output. As a result, this system is characterized by most, if not all, of the same disadvantages as projector 100, described above and with respect to FIG. 1.

In U.S. Patent Application Publication 2008/027317 (hereinafter referred to as the "317 application"), a scanning projector scans a first light signal over a image points in a sample region, wherein the first light signal is also characterized by a wavelength that is long enough to be absorbed by blood (e.g., 740 nm). The first light signal is reflected from the image points and detected at a photodetector that is selectively sensitive to the wavelength of the first light signal. When the output of the photodetector indicates the presence of a vein at an image point, a second light signal of a visible wavelength is added to the first light signal. The two light signals are combined using a free-space optical system based on "dielectric mirrors."

Unfortunately, the system disclosed in the 317 application also has several drawbacks. First, in contrast to the present invention, free-space optics are used to combine the light signals. Second, this system also relies on direct modulation of the intensities of the laser sources. As a result, the system disclosed in the 317 application also has all the same disadvantages of projector 100, as described above and with respect to FIG. 1.

In contrast to the prior art, however, embodiments of the present invention are suitable for enhancing the visibility of vein structure without some of the disadvantages inherent in projectors that rely on free-space optics-based beam combiners and directly modulated laser sources.

Figure 8:
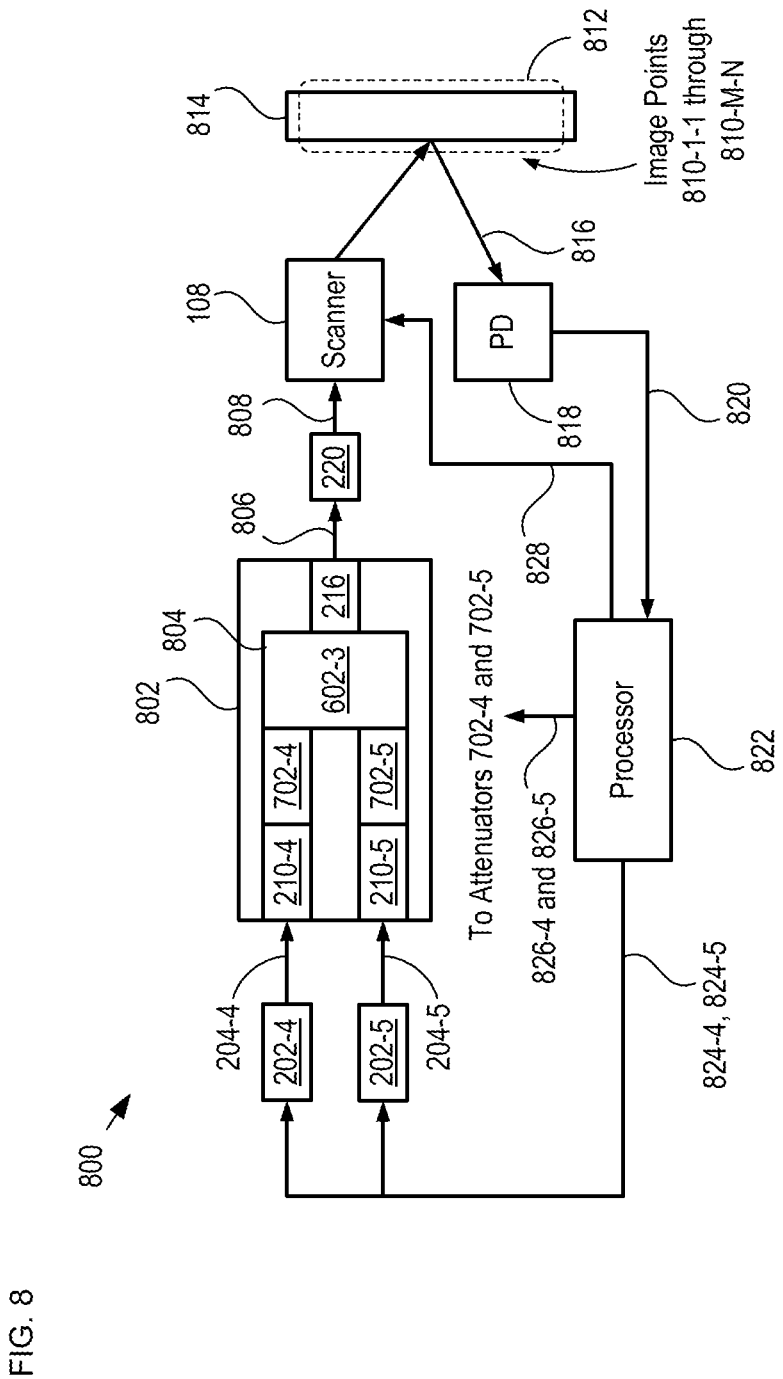
FIG. 8 depicts a schematic drawing of a scanning projector in accordance with a second alternative embodiment of the present invention.

FIG. 8 depicts a schematic drawing of a scanning projector in accordance with a second alternative embodiment of the present invention. Projector 800 is a projector for enhancing the visibility of the subcutaneous vein structure of a region of bodily tissue. Projector 800 comprises light sources 202-4 and 202-5, beam combiner 802, scanner 108, photodetector 818, and processor 822.

Projector 800 is analogous to projector 200 in that it scans an output beam having multiple light signals over an image region. Projector 800, however, scans a beam including a first signal of a first wavelength over the image region and controls the presence of a second light signal in the beam based a property of each image point in the image region. The property of each image point is determined based on reflected light of the first light signal. As a result, projector 800 projects real-time data about the image points in the image region, wherein projector 200 projects only predetermined information (e.g., video frames, still images, etc.).

Specifically, projector 800 interrogates image points in the region with a light beam comprising a first light signal of a first wavelength, which is readily absorbed by blood. The projector monitors how much of the first light signal is reflected from each image point to determine the presence of a vein at that image point. When a drop in the reflected light from an image point is detected (indicating the presence of a vein), the projector adds a second light signal of a visible wavelength to the light beam to illuminate that image point for the user. By scanning the light beams over all of the image points in the region at a sufficient rate, a real-time video image of the subcutaneous vein structure is rendered directly on the sample region.

Figure 9:
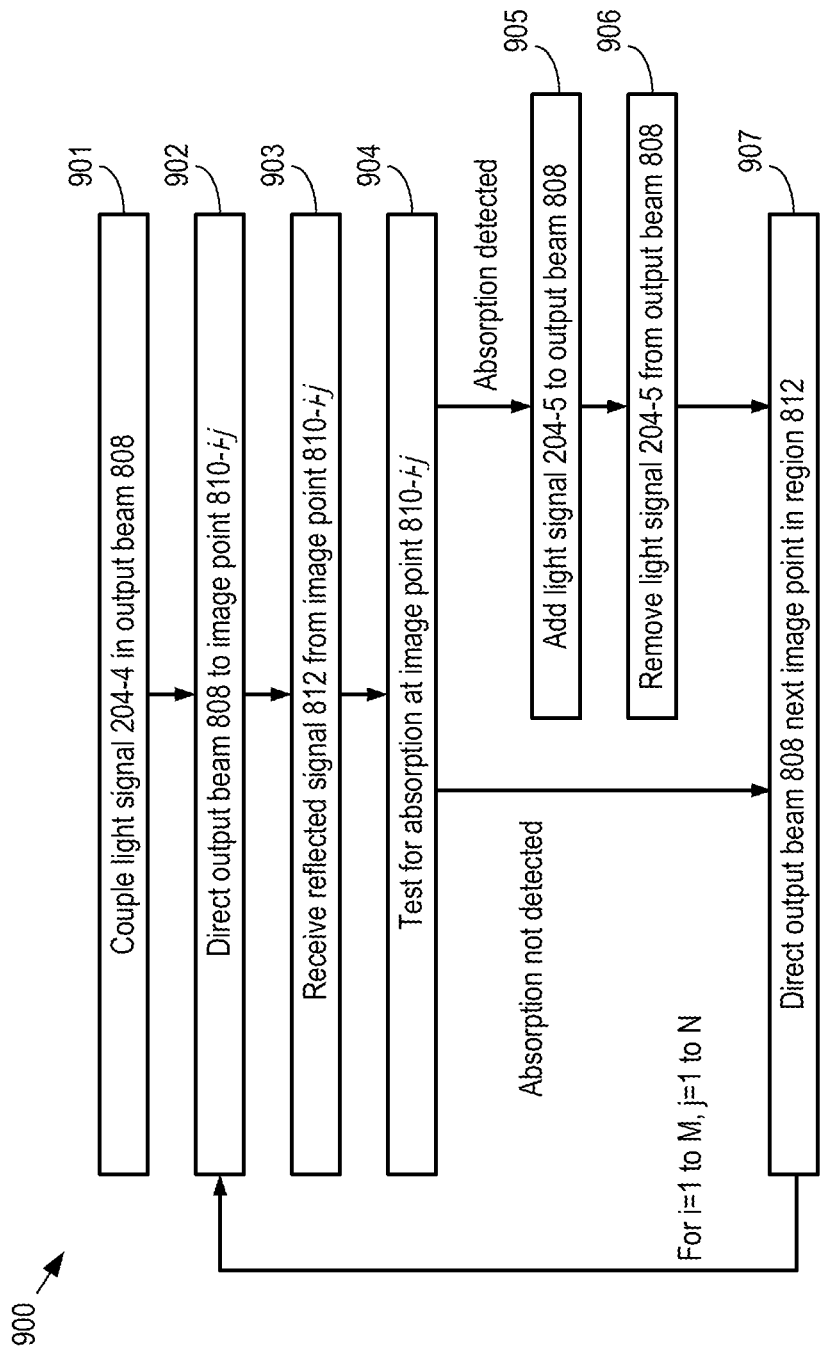
FIG. 9 depicts operations of a method for enhancing the visibility of subcutaneous vein structure in accordance with the second alternative embodiment of the present invention.

FIG. 9 depicts operations of a method for enhancing the visibility of subcutaneous vein structure in accordance with the second alternative embodiment of the present invention. Method 900 begins with operation 901, wherein light signal 204-4 is coupled into output beam 808.

Light signal 204-4 is provided to beam combiner 802 by light source 202-4, which is a laser diode that emits narrow-spectral-width light at a wavelength of approximately 740 nm. In some embodiments, light signal 204-4 is characterized by a different wavelength that is readily absorbed by blood (e.g., 850 nm, etc.). Light source 202-4 is mounted such that it is directly optically coupled with input port 210-4 of beam combiner 802.

Beam combiner 802 is analogous to beam combiner 206, described above and with respect to FIG. 2; however, beam combiner 802 is dimensioned and arranged to combine only two light signals into a composite output beam. Beam combiner 802 comprises input ports 210-4 and 210-5, attenuators 702-4 and 702-5, mixing region 804, and output port 216.

Each of input ports 210-4 and 210-5 includes a mode-matching region for enabling direct, low-loss optical coupling of light signals 204-4 and 204-5 from the output facets of light sources 202-4 and 202-4, respectively, to beam combiner 802. Input ports 210-4 and 210-5 are analogous to input ports 210-i, described above and with respect to FIGS. 5A-C.

Light signal 204-4 is conveyed to mixing region 804 via attenuator 702-4, which controls the intensity of light signal 204-4 in output beam 808 as described above and with respect to FIG. 7.

Mixing region 804 is analogous to mixing region 206; however, since projector 800 utilizes only two light signals, mixing region 804 comprises only directional coupler 602-3.

Directional coupler 602-3 is dimensioned and arranged to combine light signals 204-4 and 204-5 into composite output signal 806, as described above and with respect to FIG. 6.

Beam combiner 802 provides composite output signal 806 at output port 216, where it is collimated by lens 220 to form output beam 808.

At operation 902, scanner 108 directs output beam 808 to image point 810-$i$-$j$, wherein i=1 to M, j=1 to N, M is the number of rows of image points in region 812, and N is the number of columns of image points in region 812.

At operation 903, photodetector 818 receives reflected signal 816 from image point 810-$i$-$j$. Reflected signal 816 is a portion of output beam 808 that is reflected from the image point toward photodetector 818.

Photodetector 818 is a conventional photodetector that generates electrical signal 820, whose instantaneous magnitude is based on the instantaneous intensity of reflected signal 816. In some embodiments, photodetector 818 comprises a filter that enables photodetector 818 to selectively detect light of the wavelength of light signal 204-4. In such embodiments, the overall system signal-to-noise ratio is improved since background noise can be reduced significantly. In some embodiments, photodetector 818 comprises a filter that enables photodetector 818 to selectively detect light of a wavelength other than the wavelength of light signal 204-4. In some embodiments, photodetector 818 comprises a filter that enables photodetector 818 to detect light of only one polarization.

At operation 904, processor 822 tests reflected signal 816 for absorption of light signal 204-4 at image point 810-$i$-$j$. Due to the choice of wavelength for light signal 204-4, the presence of a vein at image point 810-$i$-$j$ induces a detectable drop in the intensity of reflected signal 816.

Processor 822 is a conventional processor suitable for executing computer programs, storing data, receiving electrical signal 820 from photodetector 818, and providing drive signals 824-4 and 824-5 to light sources 204-4 and 204-5, control signals 826-4 and 826-5 to attenuators 702-4 and 702-5, and drive signal 828 to scanner 108.

If absorption is detected at image point 810-$i$-$j$, method 200 continues with operation 905, wherein light signal 204-5 is added to output beam 808.

Light signal 204-5 is provided to beam combiner 802 by light source 202-5, which is a laser diode that emits narrow-spectral-width green light having a wavelength of approximately 532 nm. In some embodiments, light signal 204-5 is characterized by a different wavelength in the visible wavelength range. Although the human eye is most sensitive to light within the green wavelength range (i.e., the range from approximately 520 nm to approximately 570 nm), one skilled in the art will recognize that many other wavelengths of light are suitable for use in light signal 204-5, such as 633 nm, 650 nm, 670 nm, 593.5 nm, 473 nm, and 405 nm, among others. The addition of light signal 204-5 to output beam 808 while it is directed at image point 812-$i$-$j$ enhances the visibility of this image point for a user.

In some embodiments, light signal 204-5 is characterized by a wavelength that is suitable for exciting a phosphor used in vision enhancement systems (e.g., night vision goggles, etc.). Such embodiments are suitable, for example, to enable medical procedures to be carried out when stealth is desired, such as on a battlefield, or in other applications wherein a medical practitioner might be wearing such vision enhancement equipment.

In some embodiments, at least one of light signals 204-4 and 204-5 is characterized by a wavelength suitable for exciting a fluorescent material or phosphor, such as a fluorescent biomarker, that is located in or on the target sample.

The presence of light signal 204-5 in output beam 808 is controlled via control signal 826-5 provided by processor 822 to modulator 714-5 of attenuator 702-5. To add light signal 204-5 to output beam 808, modulator 714-5 is driven such that substantially all of the optical energy of light signal 204-5 remains in waveguide 208-5, as discussed above and with respect to FIG. 7. To eliminate light signal 204-5 from output beam 808, modulator 714-5 is driven such that substantially all of the optical energy of light signal 204-5 couples into waveguide portion 712-5 to be lost at light dump 716-5. In some embodiments, light signal 204-5 is added to output beam 808 by directly controlling drive signal 824-5.

At operation 906, light signal 204-5 is removed from output beam 808.

At operation 907, scanner 108 indexes output beam 808 to the next image point in the scanning pattern used to interrogate region 812. In some embodiments, scanner 108 raster scans output beam 808 over the image points in region 812. In some embodiments, scanner 108 uses a non-raster scanning pattern to interrogate the image points.

Returning to operation 905, if absorption is not detected at image point 810-*i-j* during operation 205, method 900 skips operation 206 and moves directly to operation 907. As a result, image point 810-*i-j* is not illuminated by light signal 108.

Operations 902 through 907 are repeated for each i=1 to M and j=1 to N such that projector 800 repeatedly scans the entirety of region 812 at a rate that enables a visible image of the subcutaneous vein pattern in region 812 to be rendered on surface 814.

One skilled in the art will recognize, after reading this Specification, that more than two light signals can be combined via beam combiners in accordance with the present invention, to enable, for example, interrogation of region 812 with more than one wavelength of light. In some embodiments, interrogating region 812 with a plurality of wavelengths provides advantages that include: improved measurand selectivity, the ability to determine more than one measurand, and improved measurement resolution, among others. In some embodiments, the use of multiple wavelengths for interrogation enables detection of specific chemicals, nuclear material, explosive materials, surface structure in an image region, and/or sub-surface structure in an image region. Further, additional wavelengths can be included for enhancing the projected image to render additional images of, for example, surface structure in the image region, sub-surface structure in the image region, graphics, text, and the like.

Vein-imaging systems in accordance with the present invention have many advantages over vein-imaging systems known in the prior art. By directing a single, collimated light beam that both interrogates and illuminates a scan region, all optical power can be provided to a single image point at the same time and the light beam is always in focus. In addition, by using one high-sensitivity photodetector, the need to spread the reflected signal over a large array of detector pixels is obviated. As a result, the collector optics can be simpler and less expensive, no alignment is needed between the detector array and the projection system, and a higher signal-to-noise ratio can be achieved. Further, since no detector array is included, no video processing is necessary. This reduces cost and increases system speed.

High-Power Laser Projection

In some applications, such as laser-guided munitions, laser-weaponry, and the like, it is desirable to scan and/or track an object with an output beam that comprises a very high power laser beam. For example, in some cases, once a projector has identified the presence of a target material at an image point, a user might want to add a high-power laser signal to the output beam to induce an effect at that image point, such as: illuminating the image point with a targeting-laser signal to direct a laser-guided munition; inducing combustion, or other chemical change, of material at the image point to burn the wings off an insect (e.g., a mosquito, wasp, etc.), ablate cancerous tissue, or add an identifying mark to the image point.

Conventional PLC-based systems, however, are unable to handle high-power light signals, due to the fact that they require doping with impurities to affect a refractive index difference between the core and cladding of their constituent waveguides.

In contrast to the prior art, waveguides in accordance with the present invention are not doped and, therefore, can handle higher power laser signals. Beam combiners in accordance with the present invention are based on waveguide structures exhibit guiding capability based on the difference of the refractive indices of stoichiometric silicon nitride and stoichiometric silicon dioxide. As a result, projectors comprising PLC-based beam combiners in accordance with the present invention enable the inclusion of high-power laser signals in their output beams.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A scanning projector comprising:
    a first light source that provides a first light signal characterized by a first wavelength;
    a second light source that provides a second light signal characterized by a second wavelength;
    a beam combiner comprising a planar lightwave circuit including plurality of waveguides that are arranged to define a first input port, a second input port, a mixing region, and an output port, the beam combiner: (1) receiving the first light signal at the first input port, (2) receiving the second light signal at the second input port, (3) combining the first light signal and the second light signal into a composite output signal, and (4) providing the composite output signal at the output port; and
    a scanner, the scanner receiving the composite output signal from the beam combiner and scanning the composite output signal over each of a plurality of image points in a first region.

2. The projector of claim 1 wherein the planar lightwave circuit comprises a first waveguide having an inner core comprising silicon dioxide and an outer core comprising silicon nitride.

3. The projector of claim 1 wherein the planar lightwave circuit comprises a first waveguide having a core comprising silicon nitride.

4. The projector of claim 1 wherein the planar lightwave circuit comprises a first waveguide comprising:
   a first layer comprising silicon nitride; and
   a second layer comprising silicon dioxide, the second layer disposed on and in contact with the first layer, and the second layer being a TEOS-based layer.

5. The projector of claim 1 further comprising a photodetector, the photodetector being dimensioned and arranged to receive a reflected light signal from each of the plurality of image points and generate a first electrical signal based on a characteristic of the received light signal; and
   a processor that controls the second light source based on the first electrical signal.

6. The projector of claim 5 wherein the characteristic is intensity.

7. The projector of claim 5 wherein the characteristic is polarization mode.

8. The projector of claim 5 wherein the characteristic is wavelength.

9. The projector of claim 1 further comprising:
   a third light source that provides a third light signal characterized by a third wavelength; and
   a third input port, wherein the plurality of waveguides are arranged to further define the third input port, the beam combiner receiving the third light signal at the third input port and combining the third light signal into the composite output signal.

10. The projector of claim 9 wherein the first wavelength, second wavelength, and third wavelength are irregularly spaced.

11. The projector of claim 1 wherein the mixing region comprises a plurality of directional couplers that is arranged in a first arrangement comprising a tree structure.

12. The projector of claim 1 wherein the first input port includes a mode-matching region comprising (1) a first facet that is substantially mode-matched to an output facet of the first light source and (2) an interface that is optically coupled with a first waveguide of the plurality of waveguides, and wherein the input port is optically coupled with each of the first light source and the first waveguide.

13. The projector of claim 1 wherein the planar lightwave circuit further comprises a first attenuator, the first attenuator being dimensioned and arranged to control the optical power of the first light signal in the composite output signal.

14. A scanning projector comprising:
   a plurality of light sources, wherein each of the plurality of light sources provides a different one of a plurality of light signals, each of the plurality of light signals being characterized by a different wavelength, and wherein the plurality of wavelengths are irregularly spaced;
   a beam combiner comprising a planar lightwave circuit that includes a plurality of input ports, a mixing region, and an output port, wherein each of the plurality of input ports receives a different one of the plurality of light signals, and wherein the mixing region combines the plurality of light signals into a composite output signal that is provided at the output port; and
   a scanner, the scanner receiving the composite output signal from the beam combiner and scanning the composite output signal over each of a plurality of image points in a first region.

15. The projector of claim 14 wherein the mixing region comprises a plurality of directional couplers that are arranged in a tree structure.

16. The projector of claim 14 wherein the planar lightwave circuit comprises a first waveguide having a core comprising stoichiometric silicon nitride and a cladding layer comprising silicon dioxide.

17. The projector of claim 16 wherein the plurality of input ports comprises a first input port that includes (1) an end facet that is optically coupled with a first light source of the plurality of light sources and (2) an interface that is optically coupled with the first waveguide, and wherein the end facet is characterized by a first optical mode that substantially matches the output optical mode of the first light source, and further wherein the interface is characterized by a second optical mode that substantially matches the optical mode of the first waveguide.

18. The projector of claim 14 further comprising a photodetector, the photodetector being dimensioned and arranged to receive a reflected light signal from each of the plurality of image points and generate a first electrical signal based on a characteristic of the received light signal; and
   a processor that controls the second light source based on the first electrical signal.

19. The projector of claim 18 wherein the characteristic is intensity.

20. The projector of claim 18 wherein the characteristic is polarization mode.

21. The projector of claim 18 wherein the characteristic is wavelength.

22. The projector of claim 14 wherein the planar lightwave circuit further comprises a first attenuator, the first attenuator being dimensioned and arranged to control the optical power of a first light signal of the plurality of light signals in the composite output signal.

23. A method comprising:
   receiving a first light signal characterized by a first wavelength at a first input port of a beam combiner, wherein the beam combiner comprises a planar lightwave circuit that includes the first input port and a second input port, a mixing region, and an output port;
   receiving a second light signal characterized by a second wavelength at the second input port;
   combining the first light signal and the second light signal in a composite output signal that is provided at the output port; and
   scanning the composite output signal over a first region.

24. The method of claim 23 further comprising providing the beam combiner such that the first input port includes a mode-matching region, the mode-matching region having (1) an end facet characterized by a first optical mode that substantially matches the output optical mode at an output facet of a first light source that provides the first light signal and (2) an interface characterized by a second optical mode that substantially matches the optical mode of a first waveguide, the planar lightwave circuit comprising the first waveguide.

25. The method of claim 23 further comprising:
   providing the beam combiner such that the planar lightwave circuit includes an attenuator; and
   controlling the attenuator to control the output power of the first light signal in the composite output signal.

26. The method of claim 23 further comprising:
   directing the composite output signal at a first image point in the first region;
   generating a first electrical signal that is based on a first reflected light signal reflected from the first image point, wherein a first characteristic of the first reflected light signal is based on a first property of the first image point; and
   controlling the second light signal based on the first characteristic.

27. The method of claim 26 wherein the second light signal is controlled such that the second light signal has a first magnitude when the first characteristic has a first value and a second magnitude when the first characteristic has a second value that is different than the first value.

28. The method of claim 26 further comprising:
- directing the composite output signal at a second image point in the first region;
- generating a second electrical signal that is based on a second reflected light signal reflected from the second image point, wherein a second characteristic of the second reflected light signal is based on a second property of the second image point; and
- controlling the second light signal based on the second characteristic.

* * * * *